(12) United States Patent
Riza et al.

(10) Patent No.: US 9,204,883 B1
(45) Date of Patent: Dec. 8, 2015

(54) CLAMP

(71) Applicant: R-Med, Inc., Oregon, OH (US)

(72) Inventors: Erol D. Riza, Rossford, OH (US); Cosme Ribe, Woodville, OH (US)

(73) Assignee: R-Med, Inc., Oregon, OH (US)

( * ) Notice: Subject to any disclaimer, the term of this patent is extended or adjusted under 35 U.S.C. 154(b) by 278 days.

(21) Appl. No.: 13/738,038

(22) Filed: Jan. 10, 2013

Related U.S. Application Data

(60) Provisional application No. 61/586,319, filed on Jan. 13, 2012.

(51) Int. Cl.
*A61B 17/122* (2006.01)
*A61B 17/42* (2006.01)
*A61B 17/44* (2006.01)

(52) U.S. Cl.
CPC ............ *A61B 17/122* (2013.01); *A61B 17/42* (2013.01); *A61B 17/1227* (2013.01); *A61B 17/44* (2013.01)

(58) Field of Classification Search
CPC .. A61B 17/122; A61B 17/12; A61B 17/1227; A61B 17/42; A61B 17/44
USPC ............................................. 606/120; 81/461
See application file for complete search history.

(56) References Cited

U.S. PATENT DOCUMENTS

| | | | |
|---|---|---|---|
| 1,397,876 A * | 11/1921 | Meldal | 411/427 |
| 2,686,520 A * | 8/1954 | Jarvis et al. | 606/120 |
| 4,026,294 A | 5/1977 | Mattler | |
| 4,212,303 A | 7/1980 | Nolan | |
| 4,428,374 A | 1/1984 | Auburn | |
| 4,572,181 A | 2/1986 | Mattler | |
| 4,648,401 A | 3/1987 | Mattson | |
| 4,716,886 A | 1/1988 | Schulman | |
| 4,781,188 A | 11/1988 | Collins | |
| 4,856,517 A | 8/1989 | Collins | |
| 4,870,965 A | 10/1989 | Jahanger | |
| 4,938,215 A | 7/1990 | Schulman | |
| 5,009,657 A | 4/1991 | Cotey | |
| 5,127,915 A * | 7/1992 | Mattson | 606/120 |
| 5,190,556 A | 3/1993 | Hessel | |
| 5,281,228 A | 1/1994 | Wolfson | |
| 5,415,665 A | 5/1995 | Hessel | |
| 5,423,831 A | 6/1995 | Nates | |
| 5,462,555 A | 10/1995 | Bolanos | |
| 5,520,699 A | 5/1996 | Hessel | |
| 5,575,796 A | 11/1996 | King | |
| 5,584,840 A | 12/1996 | Ramsey | |
| 5,613,655 A | 3/1997 | Marion | |
| 5,667,516 A | 9/1997 | Allen | |
| 5,676,672 A | 10/1997 | Watson | |
| 5,697,938 A | 12/1997 | Jensen | |

(Continued)

*Primary Examiner* — Kathleen Holwerda
(74) *Attorney, Agent, or Firm* — Emch, Schaffer, Schaub & Porcello, Co., L.P.A.

(57) ABSTRACT

A clamp having a first leg and a second leg where the first and second legs have a first end and a second end. A biasing means is secured to the second ends of the first and second legs. The biasing means holds the first ends of the first and second legs in a spaced apart relationship. A locking means having a rotatable locking flange is positioned on the first end of the first leg. A projection is positioned on the first end of the second leg. The projection is disposed to be in alignment with the locking means when the first end of the second leg is advanced to a position adjacent the first end of the first leg. The rotatable locking flange is rotatable to engage the projection to secure the second leg in a position adjacent the first leg.

6 Claims, 7 Drawing Sheets

(56) References Cited

U.S. PATENT DOCUMENTS

| | | |
|---|---|---|
| 5,713,912 A | 2/1998 | Porter |
| 5,797,922 A | 8/1998 | Hessel |
| 5,817,103 A | 10/1998 | Bell |
| 5,913,862 A | 6/1999 | Ramsey |
| 5,925,052 A | 7/1999 | Simmons |
| 5,938,666 A | 8/1999 | Reynolds |
| 5,947,980 A | 9/1999 | Jensen |
| 5,997,548 A | 12/1999 | Jahanger |
| 6,348,057 B1 | 2/2002 | Porat |
| D456,511 S | 4/2002 | Watson, Jr. |
| D456,512 S | 4/2002 | Watson, Jr. |
| 6,421,920 B1 | 7/2002 | Jensen |
| 6,443,958 B1 | 9/2002 | Watson, Jr. |
| 6,638,282 B2 | 10/2003 | Ramsey |
| 6,682,538 B2 | 1/2004 | Qiu |
| 6,733,508 B1 | 5/2004 | Propp |
| 6,740,095 B2 | 5/2004 | Watson |
| 6,780,195 B2 | 8/2004 | Porat |
| 6,852,117 B2 | 2/2005 | Orlowski |
| 7,402,164 B2 | 7/2008 | Watson, Jr. |
| 2002/0169459 A1 | 11/2002 | Porat |
| 2002/0198535 A1 | 12/2002 | Watson, Jr. et al. |
| 2003/0069589 A1 | 4/2003 | Small |
| 2003/0074009 A1 | 4/2003 | Ramsey |
| 2004/0199178 A1 | 10/2004 | Small |
| 2004/0215211 A1 | 10/2004 | Watson, Jr. |
| 2006/0089659 A1 | 4/2006 | Small |
| 2008/0287960 A1 | 11/2008 | Watson, Jr. |

* cited by examiner

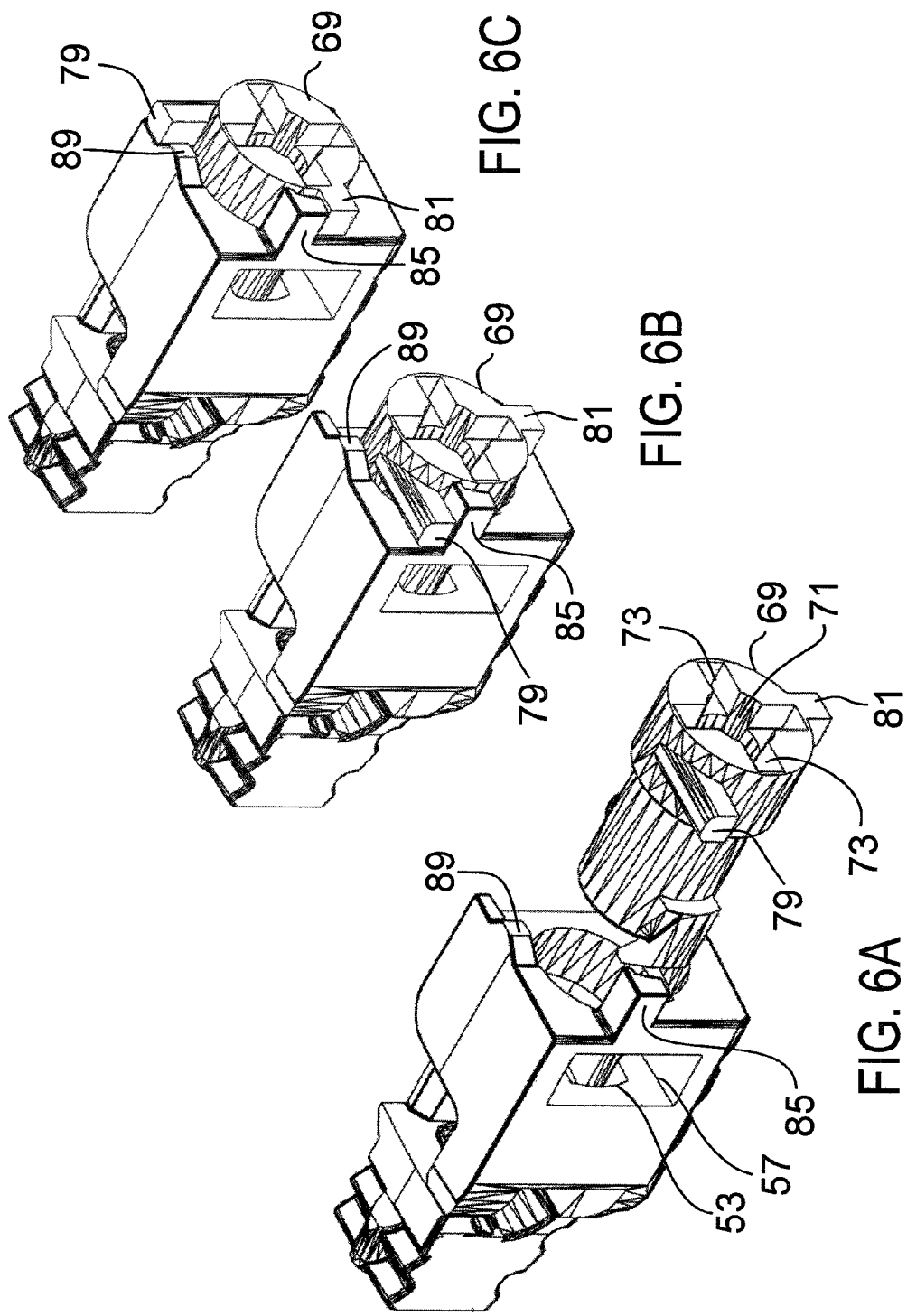

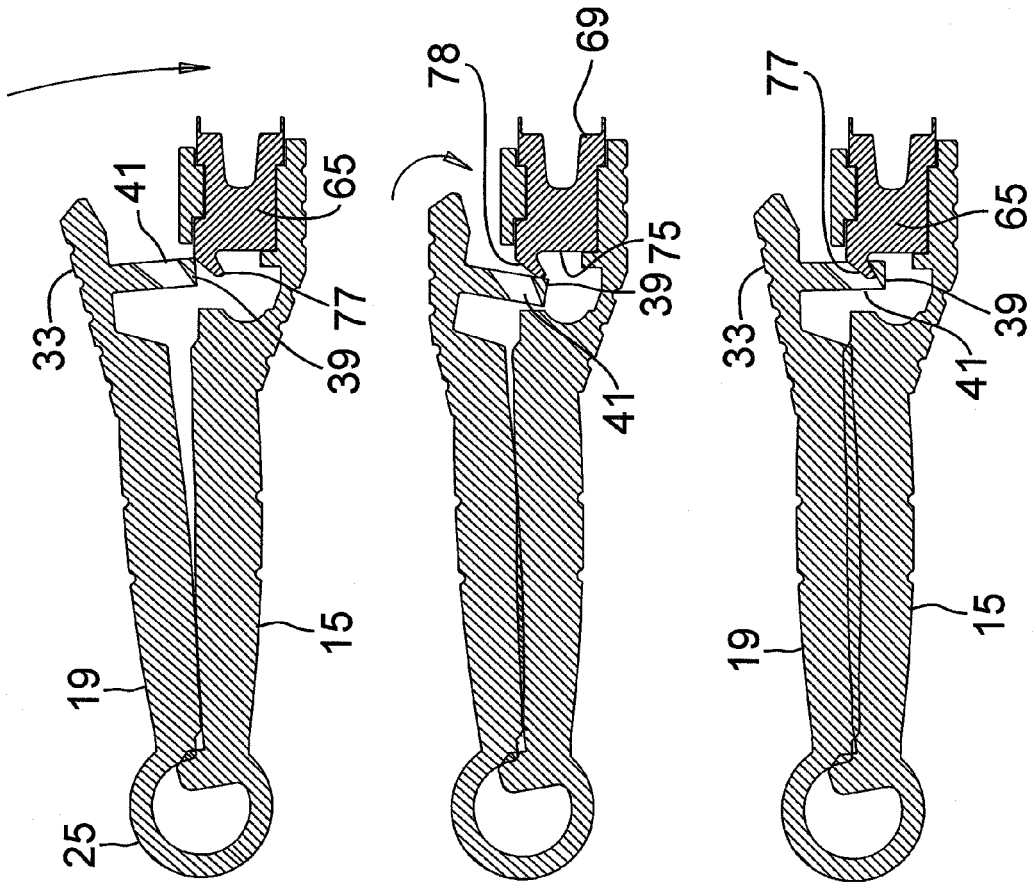

CLAMP

CROSS REFERENCE TO RELATED APPLICATIONS

This application claims the benefit of provisional patent application No. 61/586,319 filed Jan. 13, 2012.

TECHNICAL FIELD

The invention relates to a clamp that is particularly suited for use in the medical field. The clamp has two legs which are moveable into a clamping position to secure the material that is to be clamped. A locking device is provided on the clamp to retain the clamp in the clamping position. The clamp is particularly well suited for clamping an umbilical cord after the birth of baby. A key is provided that allows the clamp to be locked and unlocked in a user friendly fashion.

BACKGROUND OF THE INVENTION

In the medical field there are many situations where a clamp is required to apply a clamping force to various tissue. Clamps are frequently used to prevent the leakage of fluids from the tissue and it is important that the clamps be retained in a clamping position on such tissue. One particular use for such clamps is the clamping of an umbilical cord after the birth of a baby. It is important that a clamp that is used on an umbilical cord prevent the leakage of fluids from the umbilical cord once it is cut. Such clamp should also be effective for preventing the introduction of bacterial or viral agents into the baby through cut umbilical cord. Once the umbilical cord is properly healed it is necessary to remove the clamp from the baby. Although there are several clamps that have been used in the medical field and in particular with umbilical cords, where the clamp is positioned for an extended period of time and then removed after the umbilical cord heals. The prior art clamps are frequently difficult to close or latch and these prior art clamps are generally not easily removed from the healed umbilical cord. The use of the prior art clamps is made more difficult because the clamp is frequently used in an environment that is particularly slippery due to the presence of fluids during the typical delivery of a baby. Accordingly, there is a need for a medical clamp that can be used in slippery environments where the clamp can be easily positioned in a clamping orientation and locked in this position. At the present time standard care in most hospitals is that the cord clamps are removed before a baby is discharged to go home. The existing cord clamps are removed by cutting the hinge with a sharp disposable or re-usable cutter. It is also desirable to have a clamp for use in medical applications that can be easily released when it is no longer necessary to provide a clamping force to the tissue of the patient. It is also desirable to be able to remove the clamp without using a sharp cutting instrument.

SUMMARY OF THE INVENTION

The present invention is directed to a clamp having a first leg and a second leg. The first and second legs having a first end and a second end. A biasing means is secured to the second ends of the first and second legs. The biasing means acting to hold the first ends of the first and second legs in a spaced apart relationship.

A locking means is positioned on the first end of the first leg and the locking means has a rotatable locking flange.

A projection is positioned on the first end of the second leg. The projection is disposed to be in alignment with the locking means when the first end of the second leg is advanced to a position adjacent the first end of the first leg. The rotatable locking flange is rotatable to engage the projection to secure the second leg in a position adjacent the first leg.

Other objects and advantages of the present invention will become apparent to those skilled in the art upon a review of the following detailed description of the preferred embodiments and the accompanying drawings.

BRIEF DESCRIPTION OF THE DRAWINGS

FIGS. 6A, B and C are an exploded perspective view of the locking mechanism.

FIG. 7 is a cross sectional view of the clamp in the open position.

FIG. 8 is a cross sectional view of the clamp in a partially closed position.

FIG. 9 is a cross sectional view of the clamp in the closed or clamped position.

DETAILED DESCRIPTION OF THE PREFERRED EMBODIMENT(S)

The invention relates to a clamp that is designed primarily for use in medical applications. The clamp has a first and second leg that can be brought into immediately adjacent relationship to provide clamping pressure on an object such as an umbilical cord. The clamp can be used to clamp the newborn infant's umbilical cord after a live delivery to prevent blood loss as the umbilical cord dries and shrinks after the birth. It is used following birth of the baby and prior to separation of the placenta on the umbilical cord between the baby and the mother. A small stump of the cord and the clamp is left on the baby. The clamp also has a locking mechanism that releasably secures the first and second legs in clamping position. Although the clamp is particularly well suited for use in the medical field, it should be understood that the clamp can also be used for non-medical applications. The features of the invention will be more readily understood by referring to the attached drawings in connection with the following description.

Figure 1:
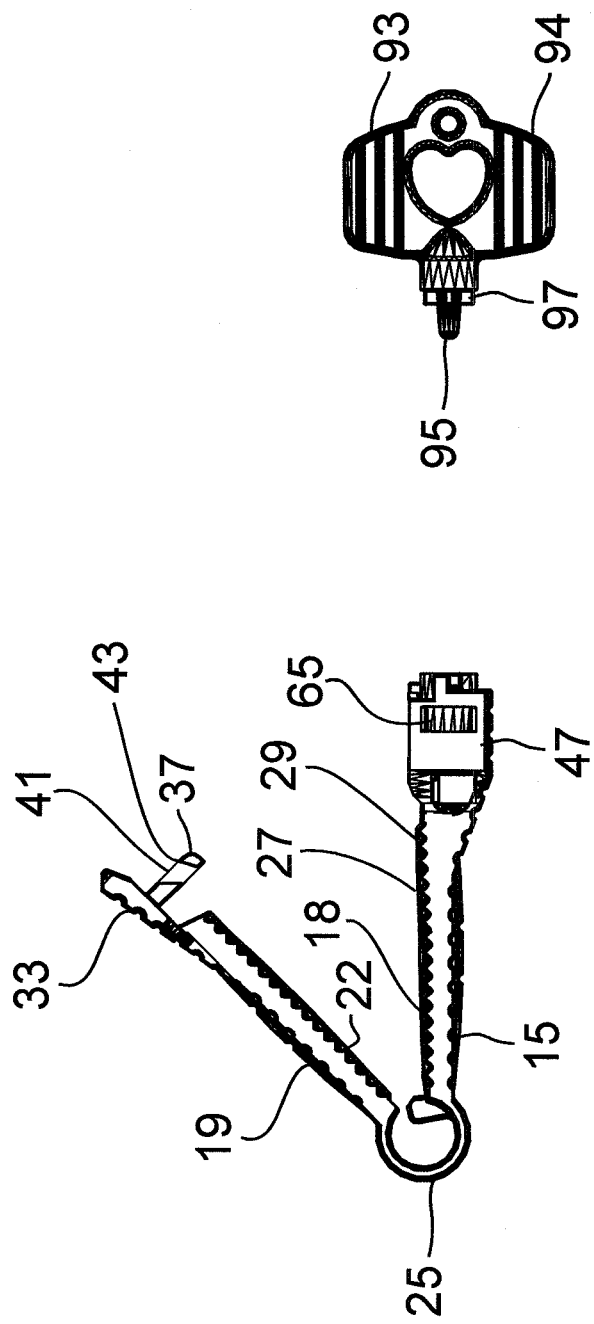
FIG. 1 is a side elevation view of the clamp of the present invention.
Figure 2:
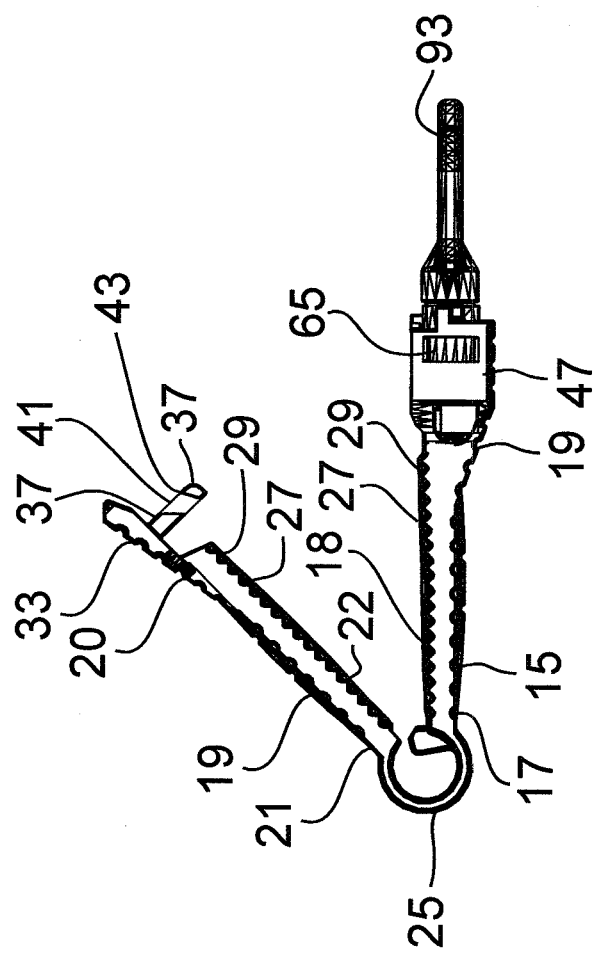
FIG. 2 is a side elevation view of the clamp with the key inserted.
Figure 3:
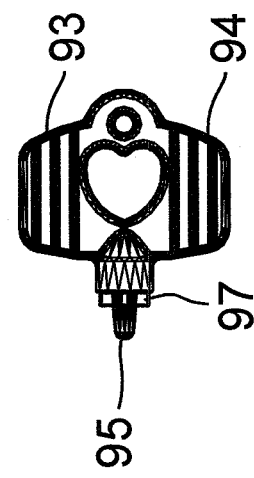
FIG. 3 is a side elevation view of the clamp in the closed position.
Figure 3:
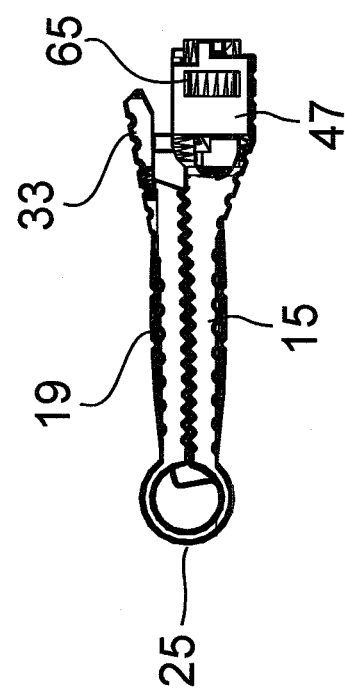
Figure 4:
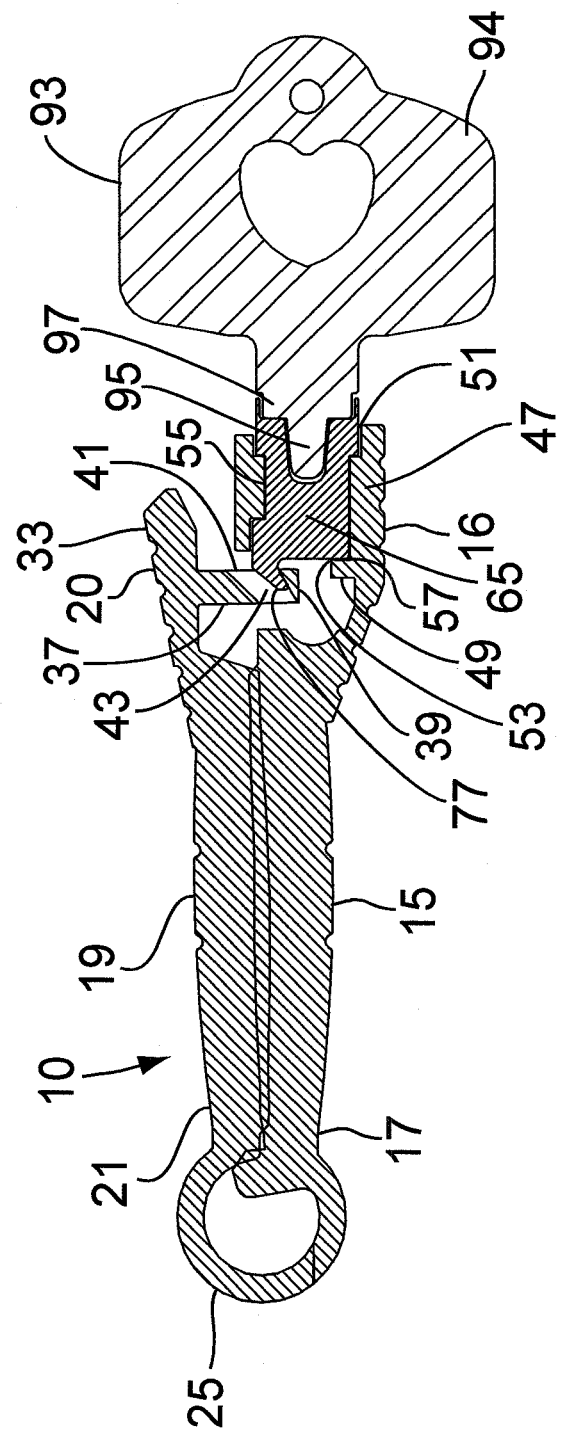
FIG. 4 is a cross section side view of the clamp in the closed position.
Figure 5:
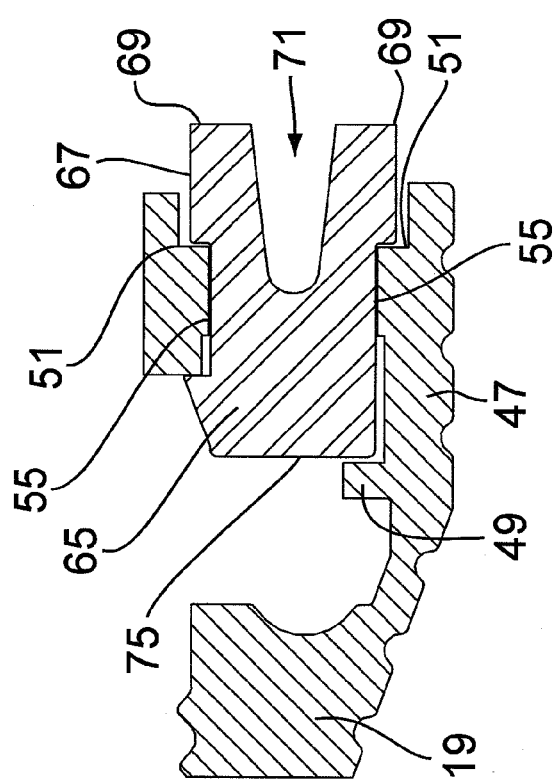
FIG. 5 is a partial cross section view of the locking mechanism for the clamp.

As shown in FIGS. 1-9, the clamp 10 has a first leg 15 having a first end 16 and a second end 17. The second leg 19 of the clamp has a first end 20 and a second end 21 that are disposed in opposed relationship as to the first leg 15. Biasing means 25 connects the first leg 15 to the second leg 19. The biasing means 25 is a generally circular piece of material that functions as a hinge and a spring to bias the second leg 19 away from the first leg 15. The first leg 15, second leg 19 and biased means 25 are usually formed of a plastic material. The first leg 15 has a first surface 16 and the second leg 19 has a first surface 22. The first surface on the first leg and the first leg on the second leg are disposed in an aligned opposed relationship with each other. A raised clamping ridge 27 is positioned on the first surface on the first and second legs. The clamping ridge is preferably positioned in the center of the first surface on the first and second legs. The raised clamping ridge 27 extends essentially from the first end to the second end of the first and second legs. A plurality of serrations 29 are positioned on the first surfaces of the first and second legs along the sides of the raised clamping ridge 27.

A biasing surface 33 is disposed on the second end 21 of the second leg 19. The biasing surface 33 positioned on the side of the second leg that is spaced apart from the raised clamping ridge 27. A projection 37 extends from the first end 20 of the second leg 19. The projections extend from the side of the second leg that is opposite to the biasing surface 33. The projection 37 extends form the first end 20 of the second leg 19 in a direction towards the first leg 15. The end 39 of the projection 37 that is spaced apart from the second leg 19 defines an angled slot 41. The angled slot defines an opening 43.

The first end 16 of the first leg 15 defines a chamber 47 having a generally circular cross sectional shaped interior opening 57. A retaining flange 49 is positioned on the end of the chamber 47 that is spaced apart from the end of the first leg 15. A shoulder 51 is defined on the end of the chamber 47 that is adjacent the end of the first leg 15. A raised projection 55 is formed in the chamber 47 adjacent the shoulder 51. The raised projection 55 extends into the interior opening 57 formed in the center of the chamber 47. A keyway 53 is formed in the interior opening 57 of the chamber 47.

A locking means 65 is rotatably positioned in the chamber 47. The locking means 65 has a generally cylindrical shape that is designed to be received in the interior opening 57 of the chamber 47. A retaining boss 67 is formed on the locking means 65. The retaining boss 67 is designed to engage the shoulder 51 on the chamber 47. The first end 69 of the locking means 65 defines an aperture 71 and a plurality of indentations 73 positioned on the first end 69 adjacent the aperture 71. Positioned on the second end 75 is a locking flange 77. The locking flange is disposed at an angle that allows the locking flange 77 to be in alignment with the angled slot 41 on the projection 37. The locking flange 77 is disposed on the locking means 65 to be positioned in alignment with the keyway 53 in the chamber 47. The locking means 65 has a locking shoulder 79 and a locking stop 81 that extend outwardly from the retaining boss 67 on the locking means 65. The locking shoulder 79 and locking stop 81 extend in a direction radially outwardly from the retaining boss 67. A limit stop 85 extends from the chamber 47 in a direction away from the end of the second leg 19. The limit stop 85 is disposed to be positioned between the locking shoulder 79 and the locking stop 81 on the locking means 65. The limit stop 85 limits the degree of rotation for the rotatable locking means 65. The end of the locking means 65 also has a detent 89 that is disposed to engage the locking shoulder 79 on the locking means 65. The detent 89 also functions to retain the locking shoulder 79 in a locking position where the locking flange 77 is disposed in a position where it can engage the angled slot 41 on the projection 37.

A key 93 having a shaft 95 and a plurality of drive projections 97 is provided to rotate the locking means 65. The shaft 95 on the key is disposed to be positioned in the aperture 71 of the locking means 65. The plurality of drive projections 97 are disposed to be in alignment with and engage the plurality of indentations 73 when the shaft 95 is fully positioned in the aperture 71. The relationship of the shaft and the plurality of drive projections with the mating aperture and plurality of indentations on the locking means 65 allows the key 93 to be utilized to rotate the locking means 65. The key has an enlarged handle 94 that is provided to give increased leverage for the key to rotate the locking means 65.

In operation the clamp 10 is normally used in the medical field to provide a clamping force to various areas of a patient's anatomy. In particular, the clamp is particularly well suited for use as a clamp on umbilical cords on newborn babies. The function of the clamp will described in connection with use on an umbilical cord, but it should be understood that the clamp can be used other purposes.

The umbilical cord or other item that is to be clamped is positioned between first surface 18 of the first leg 15 and the first surface 22 of the second leg 19. The biasing means 25 will displace the second leg 19 from the first leg 15 to allow the umbilical cord to be so positioned in the clamp. The biasing surface 33 on the first end 20 of the second leg 19 is then advanced in a direction towards the first leg 15. When the second leg 19 is brought into immediately adjacent relationship with the first leg 15 the raised clamping ridges 27 on the first and second legs will engage the umbilical cord and provide a clamping force against the umbilical cord. The biasing means 25 acts to bias the second leg 19 away from the first leg 15 and to retain the clamping force on the umbilical cord it is necessary to secure the second leg in a position adjacent the first leg.

As shown in FIGS. 7-9, the clamp can easily be positioned in the closed or clamped position. The end 39 of the projection 37 is brought into position adjacent the locking flange 77 on the locking means 65. Pressure is applied to the biasing surface 33 in a direction towards the locking flange 77. The pressure causes the end 39 on the projection 37 to advance along the angled surface 78 of the locking flange. As the end 39 is advanced it is displaced in a direction away from the locking means 65. Once the end 39 advances past the angled surface 78 of the locking flange 77, the locking flange is in alignment with the angled slot 41 on the projection 37. The projection has sufficient resiliency that the projection moves in a direction towards the locking means 65 to its original undisplaced orientation and into the slot 41. When the lock flange 77 is positioned in the angled slot 41 the first 15 and second 19 legs are held in a clamped relationship. The first and second legs will remain in this position until the locking flange 77 is released from the angled slot 41. The clamp is placed in the locked position by just applying a force on the biasing surface 33 which makes it easy to position and close the clamp 10 in difficult, slippery conditions.

An alternative way can be used to retain the second leg 19 in the clamping position. In this operation the locking means 65 is rotated by the key 93 to bring the locking flange 77 into alignment with the angled slot 41 on the end 39 of the projection 37. As the projection 37 is secured to the second leg 19 the locking flange when it engages the angled slot 41 acts to retain the second leg 19 in the clamping position. The locking flange 77 moves through the opening 43 in the projection 37 to allow the locking flange to engage the angled slot 41. The detent 89 on the chamber 47 retains the locking shoulder 79 in position where the locking flange 77 is in engagement with the angled slot 41. The locking means 65 is rotated by the key 93. The shaft 95 of the key is positioned in the aperture 71 of the locking means to properly position the key. The plurality of drive projections 97 on the key 93 are brought into alignment with the plurality of indentations 73 on the locking means 65. The plurality of projections engages the plurality of indentations to provide an engagement between the key and the locking means. The handle 94 of the key 93 provides leverage that allows the locking means 65 to be rotated in a clockwise direction to advance the locking shoulder 79 past the detent 89. The locking shoulder 79 is retained by the detent in a locked position with the locking flange 77 in positioned in the angled slot 41 on the projection 37. This location for the components keeps the clamps securely engaged in the clamped position.

If it is desired to release the clamping pressure provided by the clamp 10 the key 93 can be used to rotate the locking means 65 in a counter clockwise direction. With this rotation the locking means 65 must be rotated with sufficient force to advance the locking shoulder 79 past the detent 89. The locking means 65 is rotated in a counter clockwise direction until the locking shoulder 79 is in position against limit stop 85 on the chamber 47. When the locking means 65 is in this location the locking flange 77 is no longer in engagement with the angled slot 41 on the projection 37 and the second leg 19 will be advanced in a direction away from the first leg 15 by the force provided by the biasing means 25. Accordingly, the clamping force of the clamp 10 is released and the tissue being clamped is no longer subjected to the clamping force of the first and second legs. The rotation of the locking means 65 is constrained by the limit stop 85 that is positioned on the chamber 47. The limit stop 85 is designed so that the locking shoulder 79 is in engagement with the limit stop when the clamp 10 is in the unlocked position. When the clamp is in the locked positioned the locking stop 81 on the locking means 65 is in engagement with the limit stop 85. The limit stop 85 allows the locking means 65 to be rotated only through the arc where either the locking shoulder 79 or the locking stop 81 come into engagement with the limit stop 85. Thus, the locking means can be rotated between a locked and unlocked position for the first and second legs of the clamp 10.

It is also possible to open the clamp 10 by cutting the biasing means or hinge 25 with a sharp instrument. The ease of opening the clamp should result in using a sharp instrument only in cases where the key 93 is not available or in an emergency. It is preferred that the safer methods be used to operate the clamp and that sharp instruments are kept away from the patient. The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:
1. A clamp comprising:
   a first leg and a second leg, the first and second legs having a first end and a second end;
   a biasing means secured to the second ends of the first and second legs, the biasing means acting to hold the first ends of the first and second legs in a spaced apart relationship;
   a locking means positioned on the first end of the first leg, the locking means having a rotatable locking flange, the rotatable locking flange is positioned on a cylinder that is rotatably mounted on the first end of the first leg, the locking flange having an angled surface on an end of the locking flange that is spaced apart from the cylinder;
   a resilient projection positioned on the first end of the second leg, the projection has a slot that is disposed to engage the locking flange of the locking means, the projection extending from the first end of the second leg in a direction towards the locking means, the slot on the projection being disposed to be in alignment with the locking flange of the locking means when the first end of the second leg is advanced to a position adjacent the first end of the first leg; the rotatable locking flange being rotatable to engage and disengage the projection, the angled surface being disposed to engage and displace the projection to allow the slot to align with the locking flange.

2. The clamp of claim 1 wherein the biasing means is a spring means attached to the first and second legs.

3. The clamp of claim 2 wherein the spring means is a circular spring that joins the first leg to the second leg.

4. The clamp of claim 1 wherein the cylinder has a tab that projects in a direction away from the cylinder and the first end of the first leg has a detent that is disposed to engage the tab, the detent acting to retain the locking means in a position in engagement with the projection on the first end of the second leg to retain the locking means in a locked position when the locking means has been rotated to engage the projection.

5. The clamp of claim 4 wherein the cylinder has an opening with at least one groove positioned adjacent the opening.

6. The clamp of claim 5 wherein a key having a shaft and a raised section adjacent the shaft is positioned in the opening, the raised section being disposed to engage the at least one groove whereby the key can be used to rotate the cylinder to lock and unlock the locking means.

\* \* \* \* \*